United States Patent [19]

McAleer et al.

[11] 4,288,539

[45] Sep. 8, 1981

[54] BACTERIAL OR BACTERIAL ANTIBODY ASSAY

[75] Inventors: William J. McAleer, Ambler; Henry Z. Markus, Wyncote; Roy A. Machlowitz, Glenside, all of Pa.

[73] Assignee: Merck & Co., Inc., Rahway, N.J.

[21] Appl. No.: 16,252

[22] Filed: Feb. 28, 1979

Related U.S. Application Data

[63] Continuation-in-part of Ser. No. 794,772, May 9, 1977, abandoned.

[51] Int. Cl.³ .......................... C12Q 1/04; G01N 33/00
[52] U.S. Cl. ........................................... 435/7; 435/34; 435/810
[58] Field of Search ..................... 435/7, 805, 34, 810, 435/291; 23/230 B; 424/12, 13, 92

[56] References Cited

U.S. PATENT DOCUMENTS

| | | | |
|---|---|---|---|
| 3,773,426 | 11/1973 | Mudd | 356/205 |
| 3,902,971 | 9/1975 | Fletcher et al. | 435/7 |
| 3,932,141 | 1/1976 | Becall et al. | 424/12 |
| 3,962,413 | 6/1976 | George et al. | 23/230 B |
| 4,038,147 | 7/1977 | Reno | 435/7 |
| 4,178,359 | 12/1979 | Mandabaugh et al. | 435/7 |
| 4,186,182 | 1/1980 | Ganfar et al. | 435/7 |

OTHER PUBLICATIONS

Norden et al., "Immunologic Responses to *Hemophilus Influenzae* Meningitis", *J. Pediatrics*, vol. 80, No. 2 (1972), pp. 209–214.

Norden et al., "Effect of Previous Infection on Antibody Response of Children to Vaccination with Cupsulam Polysaccharide of Haemophilus Influenzae Type B", *J. Infect. Dig.*, vol. 132, No. 1 (1975), pp. 69–74.

Iacono et al., "A Spectrophotometric Procedure for Quantitation of Antibody Directed to Bacterial Antigens", *Immunochem.*, vol. 13, (1976), pp. 235–243.

*Primary Examiner*—Thomas G. Wiseman
*Attorney, Agent, or Firm*—Donald J. Perrella; Theresa Y. Cheng; Hesna J. Pfeiffer

[57] ABSTRACT

Automated tests to evaluate the antibody titer of a sample by incubating a test sample, bacteria, and complement, and detecting bacterial growth in the incubated mixture, and to identify bacteria and its titer in a sample by incubating a test sample, bacterial antiserum, and complement, and detecting inhibition of bacterial growth in the incubated mixture. The automated tests lend themselves to diagnostic use and may be provided in the form of diagnostic test kits.

6 Claims, No Drawings

BACTERIAL OR BACTERIAL ANTIBODY ASSAY

RELATED APPLICATION

The present application is a continuation-in-part of copending application Ser. No. 794,772 filed May 9, 1977, abandon.

BACKGROUND OF THE INVENTION

To determine the immune status of an individual has heretofore required a tedious, manual procedure involving incubating bacteria, complement and anti-sera in test tubes, plating a sample of the incubated mixture on a Petri dish, and counting the colonies which develop. In addition, due to the extreme variability of the assay, it is necessary to run replicates to obtain reliable results. This causes a considerable increase in the cost of the assay.

OBJECTS OF THE INVENTION

It is an object of the present invention to provide an automated method for evaluating the antibody titer of a sample. Another object is to provide a method for evaluating the antibody titer of a sample which method involves lesser amounts of ingredients. A further object is to provide a method for evaluating the antibody titer of a sample which method does not require plating. Still another object is to provide a method for evaluating the antibody titer of a sample which method can be carried out in the original incubation container. Yet another object is to provide a method for evaluating the antibody titer of a sample which method uses only liquid media. Another object is to provide a clinical diagnostic kit for gram negative bacteria and their antibodies. These and other objects of the present invention will be apparent from the following description.

SUMMARY OF THE INVENTION

The present invention provides (1) an automated test to determine the antibody titer of a sample by incubating in a multi-well assay plate a mixture containing a test sample, the bacteria whose antibody is being evaluated in the sample, and complement, and measuring bacterial growth in the incubated mixture, and (2) an automated test for determining the identity and initial concentration of bacteria in a sample by incubating in a multi-well assay plate a mixture containing a test sample, bacterial antiserum, complement, and growth medium and measuring inhibition of bacterial growth.

DETAILED DESCRIPTION

The present invention provides an automated method to measure antibody titer in a biological sample such as, for example, serum, plasma, blood fractions, gamma globulin, and the like. The sample is mixed with a suitable complement, e.g., rabbit complement and preferably complement from baby rabbits up to about 4 weeks old, and with the bacteria whose antibody level in the sample is being measured. After incubating the mixture for a brief period of time, e.g. for from about 30 to about 50 minutes, broth is added and the mixture incubated for from about 15 to about 30 hours, preferably for from about 20 to about 24 hours, at about 37° C.

The present invention also provides an automated method to determine the identity and initial concentration of bacteria in a biological sample such as mentioned previously. The sample is mixed with antisera for the bacteria whose identity is being determined, growth medium and complement. After incubating the mixture for a short period of time, e.g. for from about 30 to about 50 minutes, broth is added and the mixture is incubated for from about 15 to about 30 hours, preferably for from about 20 to about 24 hours, at about 37° C.

The automated assay method of the present invention is applicable to antibody or bacterial determinations for all gram negative bacteria. It has particular utility in determining antibody to such pathogenic organisms as *N. meningitidis*, Salmonella, *Neisseria gonorrhea*, *Hemophilus influenza*, *E. coli* and the like, or such pathogenic organisms themselves.

The assay is carried out using standard 96-well assay plates, automatic pipetting equipment and automatic diluting equipment. In this way the assay is automated, uses lesser amounts of ingredients than conventional methods, and is faster and more accurate. The cost of the assay is reduced considerably compared to the manual method used heretofore while the precision of the assay is improved.

The method of the present invention may conveniently be carried out in a diagnostic test kit which includes, for bacterial determination, lyophilized samples of antibody to gram negative bacteria such as, for example, antibody to *E. coli*, *S. typhi*, *N. meningitidis* strains A and C, *H. influenza* and *N. gonorrhea*. Complement may be supplied either as part of the kit or may be provided by the user of the kit. Such a kit is used to determine the identity of any of the foregoing bacteria in clinical samples. This test has the advantage of excluding nonspecific effects.

The method of the present invention may conveniently be carried out in a diagnostic test kit which includes, for antibody determination, lyophilized samples of gram negative bacteria such as, for example, *E. coli*, *S. typhi*, *N. meningitidis* strains A and C, *H. influenza* and *N. gonorrhea*. Complement may be supplied either as part of the kit or may be provided by the user of the kit. This test also has the advantage of excluding nonspecific effects.

The following examples illustrate the present invention without, however, limiting the same thereto.

EXAMPLE 1

Frozen sera samples are thawed rapidly in cold tap water. Sera are heat inactivated at 56° C. for 30 minutes and kept in ice water until removed for assay. 25 microliters of the heat inactivated sera being tested are added with sterile pipette tips to each of the 12 wells in row 1 of a 96-well assay plate. These are disposable, rigid polystyrene plates, sterile and with U wells. From 8 to 96 wells/samples are used depending upon the desired accuracy. Each plate is positioned in the automatic pipetter and 0.025 ml of sterile balanced salt solution and 0.1% bovine serum albumin is added to each of the 96 wells. The plate is then positioned in the automatic diluter which is operated according to the manufacturer's instructions. This performs two-fold dilutions if 0.025 ml diluters are being used. Using a fresh disposable tray, 0.025 ml of a fresh bacterial culture of *Neisseria meningitidis* are added to each well. This preparation must contain between 15–30 fresh viable organisms/0.025 ml. Each plate is shaken for 20–30 seconds after addition of bacteria. Next, 0.025 ml of baby rabbit complement is added to each well with an automatic pipetter. The plates are shaken again for 20–30 seconds, and then incubated for 40 minutes in a water saturated 37° C. incubator. At the end of this incubation period, 0.125 ml of Mueller Hinton broth are added to each well with the automatic pipetter. This step must be carried out with a new sterile head and a new disposable plastic reservoir. The plates are incubated overnight (20-24 hours) in a 37° C. humidified 5% $CO_2$ incubator. Wells with no bacterial growth are scored as negative. Wells with bacterial growth are scored as positive. The use of a test reading mirror makes the plate reading easier. With each test the following controls are included: number of bacteria in 0.025 ml challenge; serum control; baby rabbit complement control; inactivated baby rabbit complement control; organism control and reference sera.

| Sample | Automated Titer | | Manual Petri-Dish Titer | |
|---|---|---|---|---|
| | Pre | Post | Pre | Post |
| 1 | 8 | 64 | 16 | 128 |
| 2 | 64 | 2048 | 64 | 1024 |
| 3 | 32 | 2048 | 32 | 512 |
| 4 | 2 | 256 | 2 | 256 |
| 5 | 128 | 4096 | 32 | 512 |
| 6 | 8 | 256 | 8 | 256 |
| 7 | 4 | 128 | 2 | 256 |
| 8 | 32 | 512 | 16 | 256 |

EXAMPLE 2

The following table summarizes the assay variability as a function of the number of assays per sample.

| Number of Samples | 95% Confidence limits for average log potency |
|---|---|
| 1 | ±0.692 |
| 2 | ±0.489 |
| 3 | ±0.399 |
| 4 | ±0.346 |
| 5 | ±0.309 |
| 6 | ±0.282 |
| 7 | ±0.262 |
| 8 | ±0.245 |
| 9 | ±0.231 |
| 10 | ±0.219 |

EXAMPLE 3

TEST KIT FOR ANTIBODIES

A clinical serum sample to be tested for the presence of antibodies to E. coli, S. typhi, N. meningitidis strains A and C, H. influenza and N. gonorrhea is heat inactivated at 56° C. for 30 minutes. 25 Microliters of the inactivated serum being tested is added with sterile pipette tips to each second well of row A of a 96-well assay plate. The rest of the wells of row A receive 25 microliters of sterile balanced salt solution. Each plate is positioned in the automatic pipetter and 25 microliters of sterile balanced salt solution with 0.1% bovine serum albumin is added to each of the 96 wells. The plate is then positioned in the automatic diluter which is operated according to the manufacturer's instructions. Two-fold dilutions are used. 25 Microliters of a reconstituted lyophilized bacterial culture of E. coli are added with sterile pipette tips to all wells of row 1 and 2. Row 1 contains the serum and row 2 is a bacterial growth control. Rows 3 and 4 receive S. typhi, and rows 5 and 6 receive N. meningitidis A. The bacterial preparations contain between 15-30 fresh viable organisms/25 microliters. They are supplied in the lyophilized state as part of the test kit and contain after reconstitution the required amount of bacteria. Next 25 microliters of baby rabbit complement are added to each well with an automatic pipetter. Plates are then shaken for 20-30 seconds and incubated for 40 minutes in a water saturated 37° C. incubator. Then 125 microliters of Mueller-Hinton broth are added to each well with the automatic pipetter. This step must be carried out with a new sterile head and a new disposable plastic reservoir. The plates are incubated overnight (20-24 hours in a 37° C. humidified 5% $CO_2$ incubator). If a sample of serum inhibits bacterial growth, the identity as well as the titer are determined.

EXAMPLE 4

TEST KIT FOR BACTERIA

25 Microliters of a clinical serum sample to be tested for the presence of the following bacteria: E. coli, S. typhi, N. meningitidis A and C H. influenza and N. gonorrhea is added with sterile pipette tips to each well of row A of a 96-well assay plate. Then 25 microliters of reference antisera for the tested bacteria are added to each second well of row A. Well A2 receives antiserum to E. coli, well A4 to S. typhi, etc. These antisera are part of the kit and are supplied in the lyophilized state. Each plate is positioned in the automatic pipetter and receives 25 microliters/ well of sterile balanced salt solution with 0.1% bovine serum albumin. The plate is then positioned in the automatic diluter and two-fold dilutions are performed. Next 25 microliters of baby rabbit complement are added to each well with an automatic pipetter. The plates are then shaken for 20-30 seconds and incubated for 40 minutes in a water saturated 37° C. incubator. Then 125 microliters of Mueller-Hinton broth are added to each well with the automatic pipetter. The plates are incubated overnight (20-24 hours in a 37° C. humidified 5% $CO_2$ incubator). If samples of reference sera inhibit bacterial growth this serves to establish the identity and initial concentration of the bacteria in the tested sera.

What is claimed is:

1. A method for determining the identity of a species of gram negative bacteria present in a sample comprising:
    (a) incubating in the wells of a multiwell assay plate a serially diluted mixture of the sample together with reference antiserum to that bacteria, and a complement;
    (b) adding a liquid growth medium to the wells containing the incubated mixtures resulting from step (a);
    (c) incubating the wells containing the mixtures from step (b) for a time effective to permit bacterial growth to occur; and
    (d) measuring and scoring the inhibition of bacterial growth in the liquid medium.

2. A method according to claim 1 wherein the first incubation is effected at about 37° C. in a water-saturated atmosphere for from about 30 to about 50 minutes.

3. The method according to claim 2 wherein the steps (a) to (e) are carried out in a multiwell-plate for a series of reference antisera to gram negative bacteria selected from E. coli, S. typhi, N. meningitidis, H. influenzae or N. gonorrhea.

4. The method according to claim 1 wherein the steps (a) to (d) are carried out in a multiwell plate for a series of gram negative bacteria are selected from a group consisting of *E. coli, S. typhi, N. meningitidis, H. influenzae* or *N. gonorrhea.*

5. A method of determining the antibody level to a species of gram negative bacteria present in a sample comprising:
(a) incubating in the wells of a multiwell assay plate a serially diluted mixture of the sample together with a culture of bacteria complementary to the antibody whose level is being determined, and a complement;
(b) adding a liquid growth medium to the wells containing the incubated mixtures from step (a);
(c) incubating the wells containing the mixtures from step (b) for a time effective to permit bacterial growth to occur and
(d) measuring and scoring the inhibition of bacterial growth in the liquid medium.

6. The method according to claims 1, 2 or 5 wherein the first incubation is carried out under a water-saturated atmosphere at about 37° C. and the second incubation is carried out under a humidified atmosphere containing about 5% carbon dioxide.

* * * * *